United States Patent [19]
Dill et al.

[11] Patent Number: 5,569,299
[45] Date of Patent: Oct. 29, 1996

[54] ENDOSCOPIC UROLOGICAL BIOPSY FORCEPS

[75] Inventors: Gary R. Dill, Lauderhill; Kevin F. Hahnen, Cooper City, both of Fla.

[73] Assignee: Symbiosis Corporation, Miami, Fla.

[21] Appl. No.: 397,423

[22] Filed: Mar. 1, 1995

[51] Int. Cl.$^6$ ..................................... A61B 17/32
[52] U.S. Cl. .................. 606/205; 128/751; 606/170; 606/206; 606/207; 606/208
[58] Field of Search ................. 128/751; 606/170, 606/205, 206, 207, 208

[56] References Cited

U.S. PATENT DOCUMENTS

| | | | |
|---|---|---|---|
| 2,751,908 | 6/1956 | Wallace | 128/321 |
| 2,778,357 | 1/1957 | Leibinger et al. | 128/2 |
| 2,994,321 | 5/1958 | Tischler | 606/207 |
| 4,243,047 | 1/1981 | Olsen | 128/751 |
| 4,522,206 | 6/1985 | Whipple et al. | 128/312 |
| 4,712,545 | 12/1987 | Honkanen | 128/305 |
| 5,389,104 | 2/1995 | Hahnen et al. | 606/174 |
| 5,431,674 | 7/1995 | Basile et al. | 606/170 |

Primary Examiner—Michael Powell Buiz
Assistant Examiner—Mark S. Leonardo
Attorney, Agent, or Firm—David P. Gordon

[57] ABSTRACT

An endoscopic urological biopsy forceps includes a hollow tube member with a control member extending therethrough, an actuator coupled to the proximal ends of the tube member and the control member and a jaw assembly coupled to the distal ends of the tube and control member. The jaw assembly includes a stationary jaw with an axle pin, and a movable jaw with an arcuate slot through which the axle pin extends such that the movable jaw is coupled to the stationary jaw and is movable both translationally and rotationally relative to the stationary jaw. The stationary jaw has a basket-like opening and part of the movable jaw fits inside the opening. The movable jaw has a pair of sidewalls each of which define a row of cutting teeth and a distal buck tooth which is arranged substantially perpendicular to the side walls and is angled toward the proximal end of the movable jaw. When the jaws are closed, the cutting teeth of the movable jaw are received in the opening if the stationary jaw and the buck tooth resides outside and adjacent the distal end of the stationary jaw. The movable jaw is preferably provided with a gouged interior defining a roof palate making additional room for the capture and storage of biopsy samples. The basket-like opening in the stationary jaw is preferably provided with bottom openings for fluid drainage and to accommodate larger and plural biopsy samples.

19 Claims, 6 Drawing Sheets

ENDOSCOPIC UROLOGICAL BIOPSY FORCEPS

BACKGROUND OF THE INVENTION

1. Field of the Invention

This invention relates broadly to endoscopic instruments. More particularly, this invention relates to multiple sample endoscopic urological biopsy forceps.

2. State of the Art

Endoscopic biopsy procedures are typically performed with an endoscope and an endoscopic biopsy forceps device (bioptome). Some endoscopes are rigid and relatively short and are used in conjunction with cannulas or trocar tubes. Other endoscopes have a long flexible tube carrying fiber optics and typically having a narrow lumen through which the bioptome is inserted. Which endoscope is used will depend on the location of the biopsy site. The bioptome typically includes a long flexible coil (or a relatively short rigid tube depending on Which type of endoscope or cannula is used) having a pair of opposed jaws at the distal end and manual actuation means at the proximal end. Manipulation of the actuation means opens and closes the jaws. During a biopsy tissue sampling operation, the practitioner guides the endoscope to the biopsy site while viewing the biopsy site through the fiber optics of the endoscope. The bioptome is inserted through the narrow lumen of the endoscope or through a lumen of another device such as a trocar, catheter or needle, until the opposed jaws arrive at the biopsy site. While viewing the biopsy site through the fiber optics of the endoscope, the practitioner positions the jaws around a tissue to be sampled and manipulates the actuation means so that the jaws close around the tissue. A sample of the tissue is then cut and/or torn away from the biopsy site while it is trapped between the jaws of the bioptome. Keeping the jaws closed, the practitioner withdraws the bioptome from the lumen. The biopsy tissue sample must then be removed from the jaws.

When specifically used to gather tissue samples from the bladder of a patient, the above described procedure is known as a urological biopsy procedure. A urological biopsy procedure most often involves the taking of tissue samples from within the bladder of a patient suspected of having bladder cancer. In a cancerous bladder, evidence of the cancer may be found in the form of developing cancer cells in the muscle lining the walls of the bladder. When performing a urological biopsy procedure, the practitioner must usually take multiple biopsy samples. However, since the muscle in the bladder is covered with several layers of mucosal tissue, it is often difficult for the practitioner when using conventional endoscopic biopsy inset rudiments to find and gather tissue samples. In particular, the jaws of a conventional biopsy forceps are usually not sufficiently large to cut through the mucosal tissue and obtain a muscle biopsy. Another problem encountered by the practitioner performing a urological biopsy procedure is that the muscle tissue is very tough and requires a relatively strong shearing and/or cutting force. Since there is a limit as to how strong the tools of the art can be made and still be small and flexible enough for use in a urological biopsy procedure, there is always the possibility that the endoscopic forceps will break while in use. In such a case, the end effector or distal linkage may become lodged in the bladder and will require additional procedures to remove it.

As mentioned above, a proper urological biopsy procedure usually requires the taking of several tissue samples, as many as twelve, either from the same or different biopsy sites. Unfortunately, most endoscopic biopsy instruments are limited to taking a single tissue sample, after which the device must be withdrawn from the endoscope and the tissue collected before the device can be used again to take a second tissue sample. The single-sample limitation of these endoscopic biopsy instruments is due to the limited space between the biopsy forceps jaws.

Co-owned applications Ser. Nos. 08/355,057, filed Dec. 13, 1994 and 8/189,973, filed Feb. 1, 1994 disclose biopsy instruments where several tissue samples may be stored between the jaws of the jaw assembly when in the closed position. Although these multiple sample biopsy instruments represent an improvement over the prior art, the jaw configurations disclosed therein do not specifically address the problems associated with urgical biopsy procedures of locating and cutting the tough muscle tissue in the bladder.

SUMMARY OF THE INVENTION

It is therefore an object of the invention to provide an endoscopic biopsy forceps with a jaw arrangement which can cut through both mucosal and muscle tissue, and store samples of muscle tissue.

It is also an object of the invention to provide an endoscopic urological biopsy forceps with a jaw arrangement which can sever and store multiple biopsy samples.

It is another object of the invention to provide an endoscopic biopsy forceps with a jaw arrangement in which the jaws open wide and are provided with an enhanced mechanical advantage.

It is another object of the invention to provide an endoscopic biopsy forceps with a jaw arrangement which is easy to manufacture and assemble.

It is another object of the invention to provide an endoscopic urological biopsy forceps with a jaw arrangement which has a high cutting strength.

It is still another object of the invention to provide a biopsy forceps with a jaw arrangement which has a scoop action to draw tissue into the jaws before it is severed.

In accord with these objects which Will be discussed in detail below, the endoscopic urological biopsy forceps of the invention includes a tube and a control member extending through the tube, an actuator coupled to the proximal ends of the tube and the control member, a stationary jaw coupled to the distal end of the tube and having a pin substantially perpendicular to the longitudinal axis of the tube, and a movable jaw coupled to the distal end of the control member and having an arcuate slot through which the pin extends. With the provided arrangement the movable jaw is pivotally coupled to the stationary jaw and follows an eccentric path as it is opened and closed. In addition, the movable jaw and the stationary jaw are arranged such that when they are in a closed position relative to each other they define a space in which biopsy samples are stored. Thus, the stationary jaw is preferably provided with a distal basket-like portion having a substantially open top for receiving the movable jaw and severed tissue samples and a bottom surface having a plurality of openings therein. The openings permit fluid in the obtained samples to drain through the bottom of the stationary jaw and also permit portions of the samples to protrude from the bottom of the stationary jaw so than more and larger samples may be captured. The movable jaw is substantially hollowed and forms a palate with a row of cutting teeth on each side and a distal severing tooth. When the movable jaw is in a closed position relative to the stationary jaw, the rows of cutting teeth on opposite sides of the movable jaw are located inside the open top of the stationary jaw, while the distal severing tooth is located outside the open top of the stationary jaw. The eccentric path Of the movable jaw, together with its arrangement of teeth on the sides and distal end permits the movable jaw to act as a scoop which draws tissue into the opening in the stationary jaw before and during severing of the tissue.

According to additional aspects of the invention, the distal severing tooth is substantially longer and wider than the side cutting teeth, such that the distal severing tooth has a high severing strength for cutting tough muscle tissue when taking and storing samples. Also, the tube of the urological biopsy forceps of the invention is preferably a flexible coil, while the control member is preferably a strong flexible wire coupled to a lever in the actuator. Since the coil and wire are both flexible they may be used in an endoscope having a narrow lumen or in a cannula having a distal deflector. Additional objects and advantages of the invention will become apparent to those skilled in the art upon reference to the detailed description taken in conjunction with the provided figures.

DETAILED DESCRIPTION OF THE PREFERRED EMBODIMENT

Figure 1:
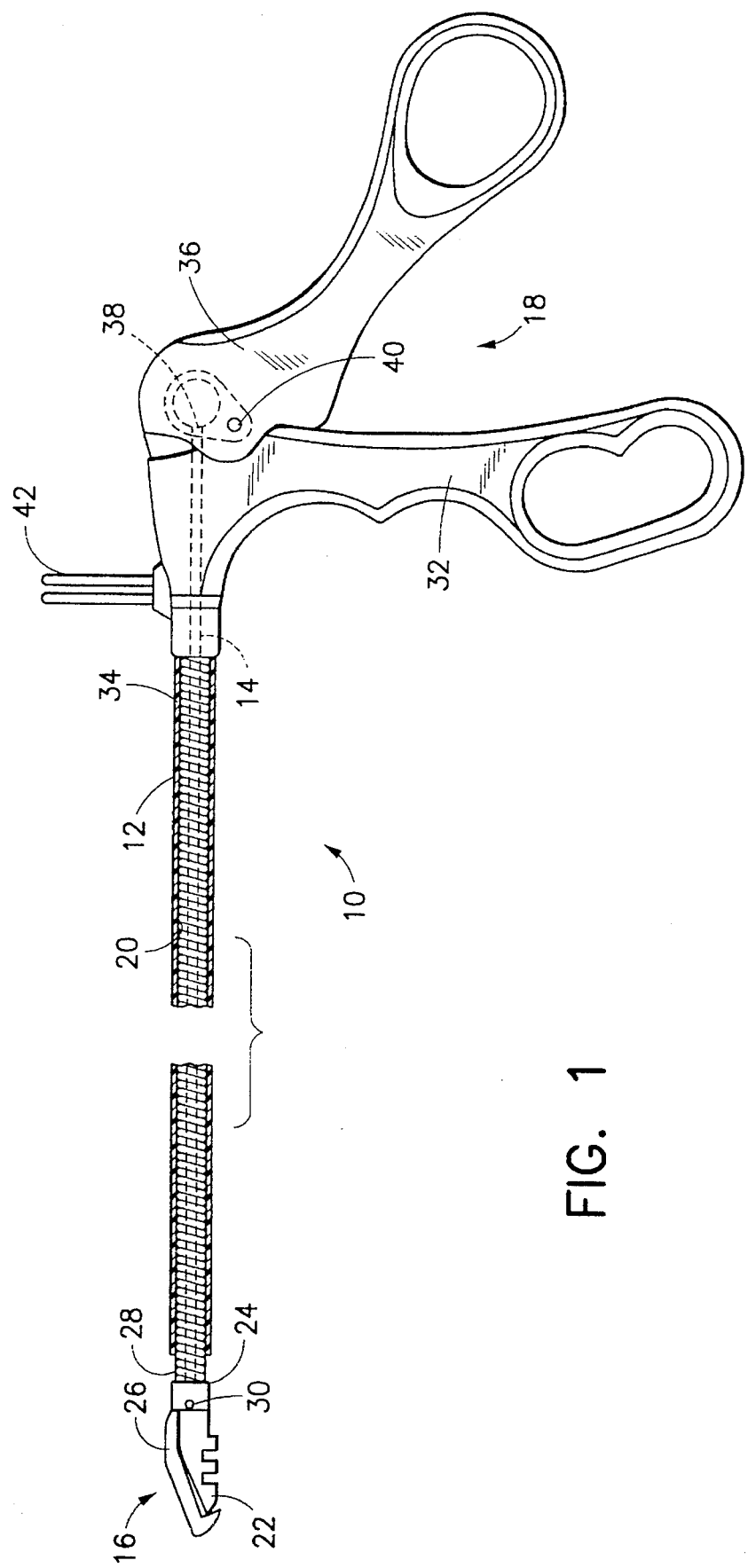
FIG. 1 is a side elevation view, partly in section, of the endoscopic urological biopsy forceps of the invention.

The endoscopic urological biopsy forceps 10 of the invention is seen in FIG. 1 and broadly includes a flexible coil 12 with a pull wire control member 14 extending therethrough, a jaw assembly 16 coupled to the distal ends of-the coil 12 and pull wire 14, and an actuator 18 coupled to the proximal ends of the coil and pull wire. The jaw assembly 16 includes a stationary jaw 22 which is coupled to the distal end 24 of the coil 12 and a movable jaw 26 which coupled to the distal end 28 of the pull wire 14 via a linkage 30. The actuator 18 includes a handle 32 which is coupled to the proximal end 34 of the coil 12 and a lever 36 which is coupled to the proximal end 38 of the pull wire 14. The lever 36 is rotatably coupled at pin 40 to the handle 32 so that movement of the lever 36 relative to the handle 32 effects a translation of the pull wire 14 relative to the coil 12. According to a presently preferred embodiment, the pull wire 14 is formed of 300 stainless steel and has a 0.022" diameter, The handle 32 may be provided with a cautery connection 42 for applying cautery current to the coil 12, and the coil 12 may be surrounded by a peripheral insulating shrink wrap layer of plastic 20. In use, the endoscopic urological forceps 10 is inserted via a cannula or other lumen or portal into the bladder of a patient (not shown) and the lever 36 is rotated relative to the handle 32 in order to impart translational movement of the pull wire 14 relative to the coil 12. The movement of the pull wire 14 is translated to a scooping movement of the movable jaw 26 relative to the stationary jaw 22 as is described more fully below.

Figure 2:
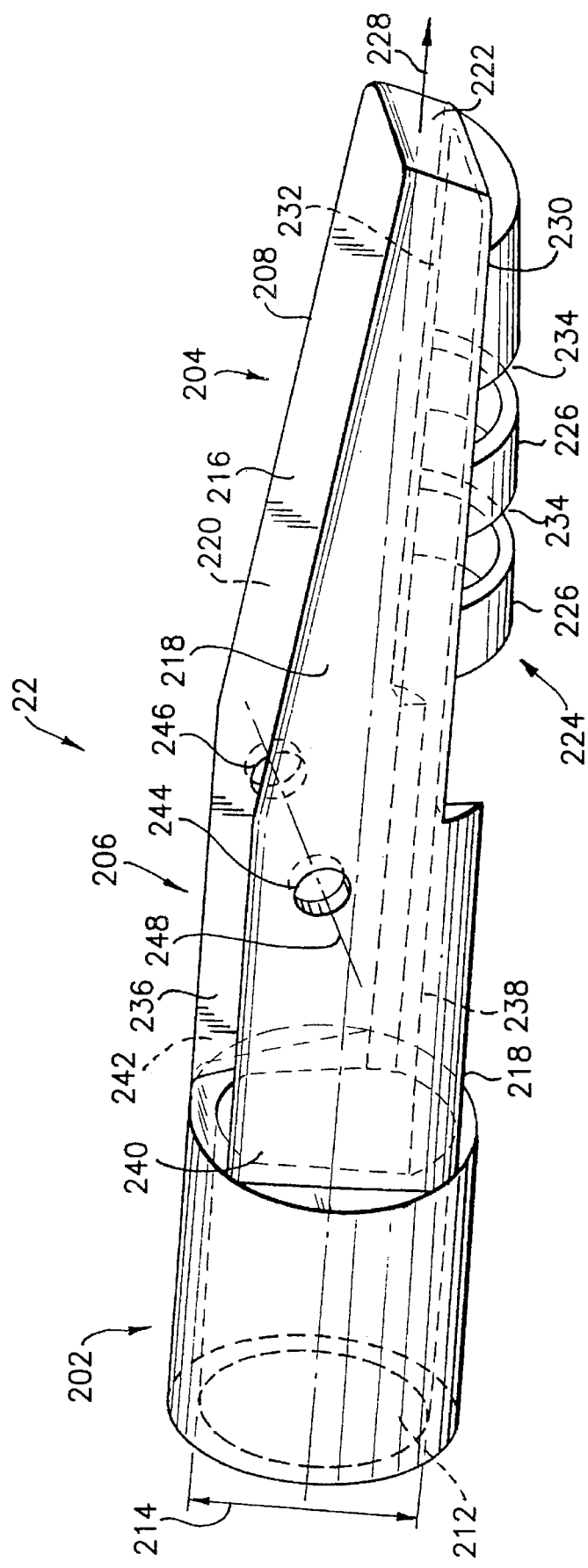
FIG. 2 is an enlarged perspective view of the stationary jaw of FIG. 1.
Figure 3:
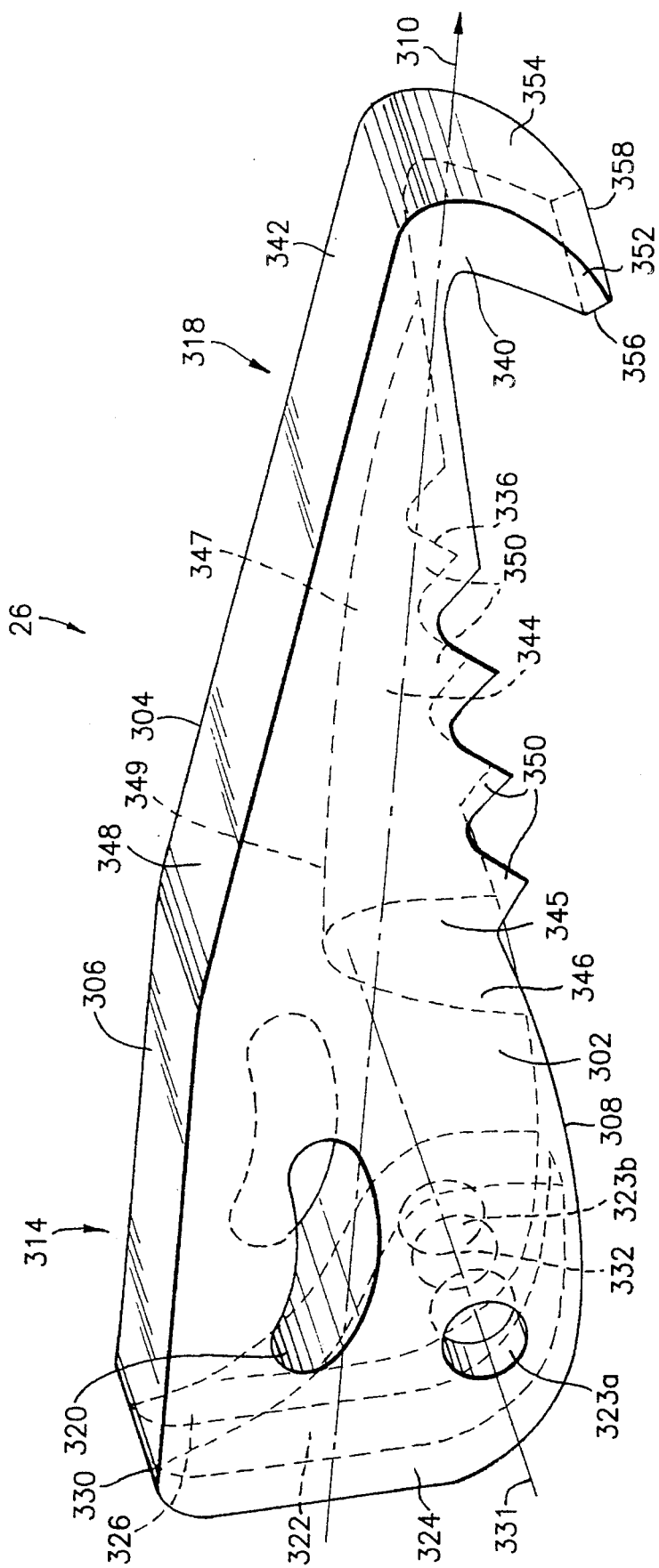
FIG. 3 is an enlarged perspective view of the movable jaw of FIG. 1.

FIGS. 2 and 3 show enlarged perspective views of the stationary jaw 22 and the movable jaw 26, respectively. Referring to FIG. 2, the stationary jaw 22 can be viewed as having a proximal shank portion 202, a distal basket portion 204, and a middle clevis portion 206, where the shank 202, basket 204, and clevis 206 are all part of an integral Stationary jaw 22. The shank 202 is preferably a hollow cylinder with a throughbore 212 having an internal diameter 214 substantially equal to the outer diameter of the flexible coil 12 of the urological biopsy forceps 10. In this manner, the distal end 24 of the coil 12 can fit into the interior of the shank 202 and the shank can be crimped onto the coil 12.

The basket portion 204 of the stationary jaw 22 has first and second walls 218, 220 and a distal wall 222 which define an opening 216 dimensioned to receive a portion of the movable jaw 26 as described below. The bottom 224 of the basket portion 204 is formed by several arcuate strips 226 which are substantially perpendicular to the longitudinal axis 228 of the stationary jaw 22, and which extend from the bottom 230 of the first side wall 218 to the bottom 232 of the second side wall 220 such that the concave portion of the strips 226 face the opening 216 of the basket 204. The arcuate strips 226 define several openings 234 24 which permit fluid flow therethrough and which are advantageously dimensioned to facilitate the storage of biopsy samples (not shown) without allowing the samples to fall through.

The clevis portion 206 of the stationary jaw 22 includes first and second parallel side walls 240, 242 which extend from the shank portion 202 to the basket portion 204 and define an open top 236 and an open bottom 238. Each side wall 240, 242 of the clevis portion 206 contains a side hole or throughbore 244, 246 which are similarly dimensioned, share a common axis 248, and are provided to receive a pin 406 (described below with reference to FIGS. 4 and 5). The presently preferred stationary jaw 22 has an overall longitudinal length of approximately 0.54 inches and a width of approximately 0.11 inches. The outer diameter of the shank portion is preferably approximately 0.11 inches, and the inner diameter of the throughbore in the shank portion is preferably approximately 0.08 inches. As seen in FIG. 2, the height of the basket portion 204 decreases distally from the clevis portion 206 to the distal wall 222 at an angle of approximately eight degrees relative to the longitudinal axis 228 of the jaw 22.

Turning now to FIG. 3, the movable jaw 26 of the invention is defined by first and second side surfaces 302, 304, top and bottom surfaces 306, 308 and has a longitudinal axis 310. The movable jaw 26 can be viewed as having a proximal mounting portion 314 and a distal cutting portion 318. The proximal mounting portion 314 includes an arcuate pin-receiving through-slot 320, a longitudinal pull wire receiving slot 322, and a pair of coaxial spaced apart pull wire coupling throughbores 323a, 323b. The arcuate pin-receiving slot describes an arc of approximately thirty degrees and traverses the entire width of the mounting portion of the jaw from the first side surface 302 to the second side surface 304. The longitudinal pull wire receiving slot 322 divides lower proximal part of the mounting portion 314 of the movable jaw into opposed walls 324, 326. The longitudinal slot 322 as shown is almost triangular in shape, and it broadens as it extends distally from just under the top surface 306 of the proximal-most end 330 of the mounting portion 314 to the bottom surface 308 of the movable jaw 26. The longitudinal slot 322 extends under the arcuate through-slot 320 but does not intersect therewith. However, the longitudinal slot 322 does intersect the throughbores 323a, 323b which extends through the opposed walls 324, 326 of the mounting portion of the jaw. In particular, the throughbores 323a, 323b, which are located near the bottom of the mounting portion 314, share a common axis 331 which is substantially perpendicular to the longitudinal axis 310 of the jaw, and intersect the longitudinal pull-wire receiving slot 322 at an intersection 332. The throughbores 323a, 323b is provided to receive a pull wire engaging pin 414 (described below with reference to FIGS. 4 and 5) so as to couple the movable jaw 26 to the distal end of the pull wire 14.

The cutting portion 318 of the movable jaw 26 can be viewed as being substantially triangular in shape (i.e., in a longitudinal cross section) with a large, muscle-cutting distal tooth 340 appended to the acutely angled distal end 342 of the jaw. The bottom surface 308 of the jaw in the cutting portion 318 is gouged with a semi-conical cut-out 344 which helps define side walls 345, 347 and a curved under-surface or palate 349. First and second rows of sharp cutting teeth 350 are cut or formed into the bottom edges of the side walls 345, 347. Each row preferably includes three triangular shaped teeth, with the rows of teeth being substantially parallel to one another, but angled relative to the longitudinal axis 310 of the jaw.

The large cutting tooth 340 at the distal-most end 342 of the cutting portion of the jaw takes the form of a large "buck tooth". The buck tooth 340 is arranged to be substantially perpendicular to the first and second rows of teeth 350 and to be substantially larger than the teeth 350. The width of the buck tooth 340 spans the width of the cutting portion 318 of the movable jaw 26, and the length of the buck tooth 340 is preferably slightly greater than the height of the stationary jaw 22 at its distal end 222 (FIG. 2). The tip 352 of the buck tooth 342 is provided with an outer surface 354 and an inner angled shearing surface 356 which meet at a cutting edge 358. The outer surface 354 of the buck tooth 342 is also generally angled toward the mounting portion 314 of the movable jaw 26 such that it forms an acute angle with the top surface 306 of the movable jaw 26. A presently preferred embodiment of the jaw 26 has an over all longitudinal length of approximately 0.43 inches and a width of approximately 0.074 inches. The proximal mounting portion has a height of approximately 0.10 inches, and the upper surface of the cutting portion of the jaw is inclined downward in the distal direction at an angle of approximately 8.6 degrees.

Comparing FIGS. 2 and 3, it will be appreciated that when the jaws are in the closed position, the basket 204 of the stationary jaw 22 and the palate 349 the movable jaw 26 form a space sufficiently large to store multiple urological biopsy samples.

Figure 4:
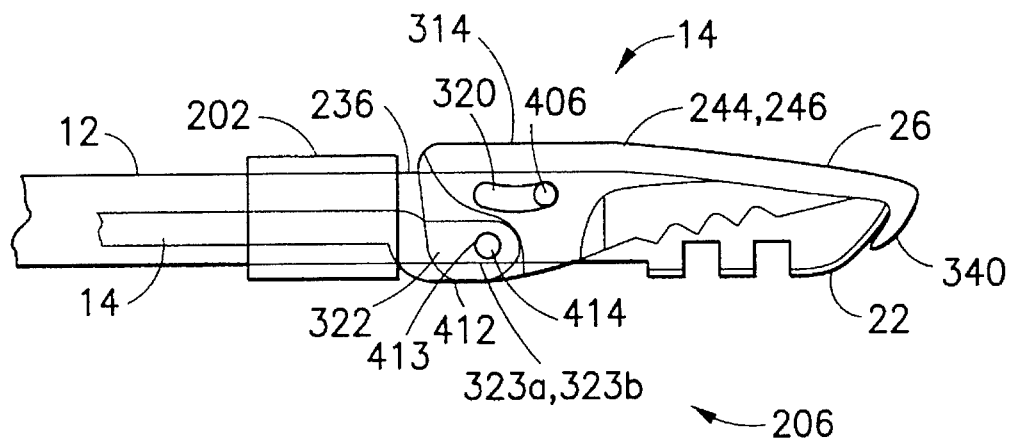
FIG. 4 is a broken transparent side elevation view in partial section of the jaw assembly of the endoscopic urological biopsy forceps of FIG. 1 in the fully closed position.
Figure 4A:
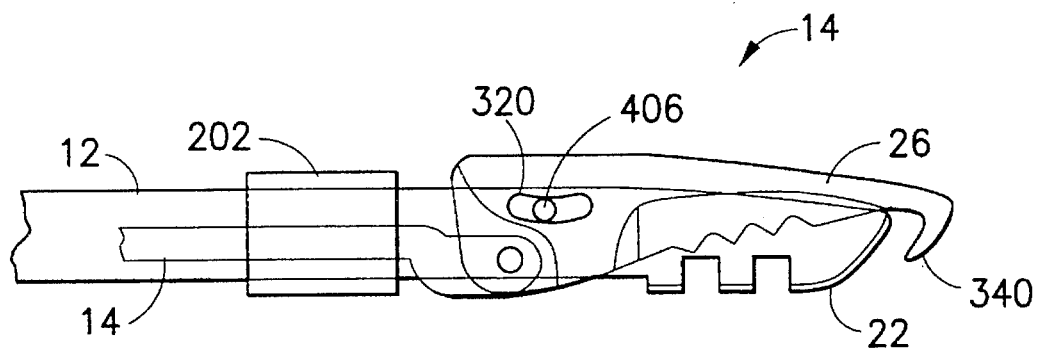
FIG. 4a is a view similar to FIG. 4 of the jaw assembly in a first intermediate position between fully closed and fully open.
Figure 4B:
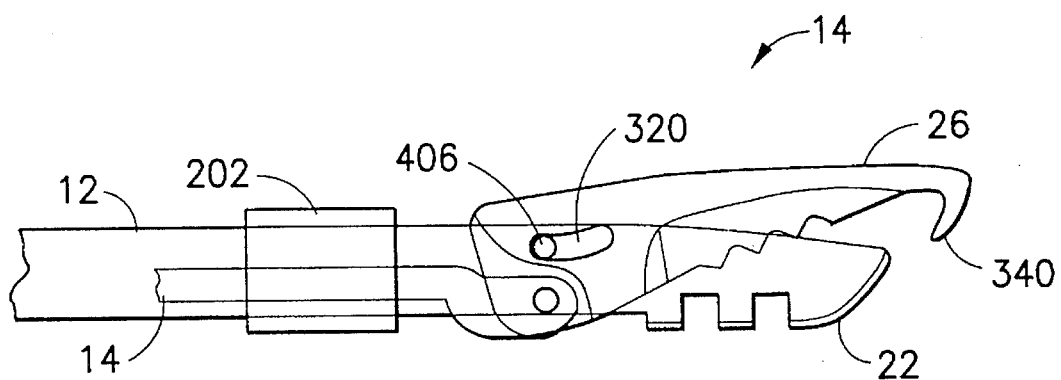
FIG. 4b is a view similar to FIG. 4 of the jaw assembly in a second intermediate position between fully closed and fully open.
Figure 5:
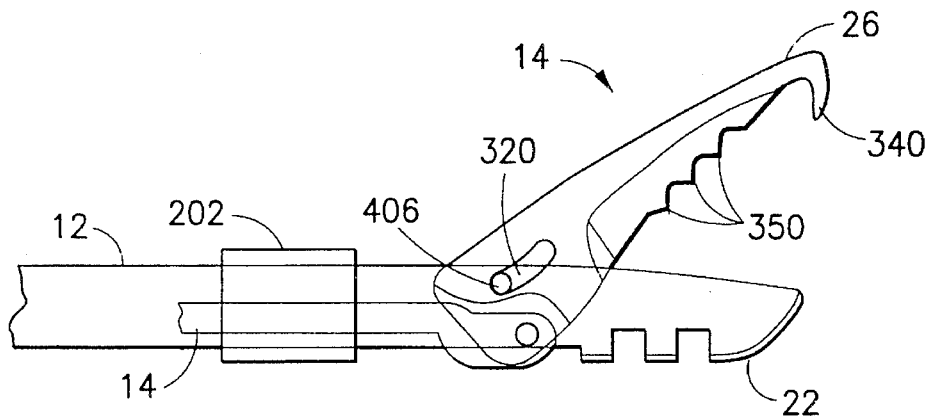
FIG. 5 is a view similar to FIG. 4 of the jaw assembly in the fully open position.
Figure 5A:
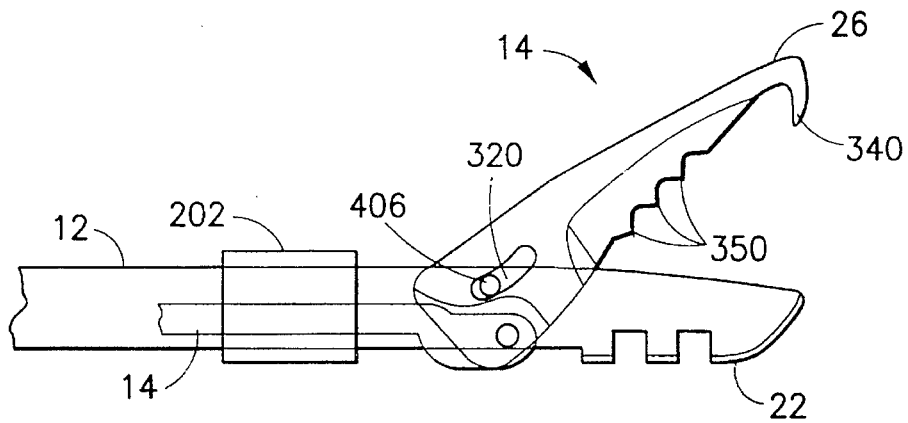
FIG. 5a is a view similar to FIG. 4 of the jaw assembly in a first intermediate position between fully open and fully closed.
Figure 5B:
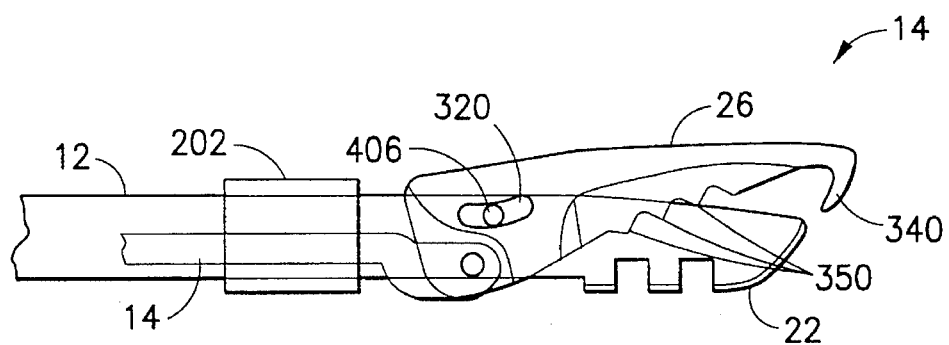
FIG. 5b is a view similar to FIG. 4 of the jaw assembly in a second intermediate position between fully open and fully closed.

The operation of the jaw assembly 14 when being opened from the fully closed position is shown in FIGS. 4, 4a, and 4b. The operation of the jaw assembly when being Closed from the fully open position is shown in FIGS. 5, 5a, and 5b. Turning now to FIG. 4, the jaw assembly 14 of the endoscopic urological biopsy forceps is shown assembled with the jaws 22, 26 in the fully closed position. As shown, the distal end of the coil 12 is fit into the shank portion 202 of the stationary jaw 22. The mounting portion 314 portion of the movable jaw 26 is then received by the top opening 236 of the clevis portion 206 of the stationary jaw 22 such that the side holes 244, 246 in the stationary jaw 22 are aligned with the arcuate slot 320 in the mounting portion 314 of the movable jaw 26. A cylindrical pin 406 is placed into the one of the holes 244, 246, through the arcuate slot 320, and into the other hole and fastened to the stationary jaw 22 by any known means in the art. In this manner, the arcuate slot 320, and hence the movable jaw 26 is permitted to ride on the pin 406. A flattened plate-like terminal portion 412 of the pull wire 14 having a hole 413 therein is located in the longitudinal slot 322 of the mounting portion 314 of the movable jaw 26. The hole 413 is aligned with the throughbores 323a, 323b of the mounting portion 314 of the movable jaw 26, and a second cylindrical pin 414 is placed through the throughbores 323a, 323b in the jaw 26 and the hole 413 in the terminal portion 412 of the pull wire 14 in order to connect the pull wire to the immovable jaw.

From the foregoing, and with reference to FIGS. 1 and 4, it will be appreciated that movement of the lever 36 relative to the handle 32 (see FIG. 1), will cause a translational movement of the pull wire 14, which in turn will cause the movable jaw 26 to ride over the pin 406. Since the slot 320 in the jaw 26 which receives the pin 406 is arcuate, the movable jaw will tend to rotate and translate relative to the stationary jaw 22.

Starting from the position shown in FIG. 4, which is the fully closed position which the jaws assume when the lever of the actuator is pressed closest to the handle, FIGS. 4a and 4b illustrate how the movable jaw translates and rotates to the fully open position shown in FIG. 5. It should be noted that when the jaws are fully closed, the movable jaw 26 is located such that the pin 406 is at the distal end of the slot 320. As seen in FIG. 4a, when the pull wire 14 is moved in the distal direction, the jaw 26 is also moved distally with the slot 320 sliding over the pin 406. Due to the curvature of the slot 320, the jaw 26 is also slightly rotated away from the jaw 22. As the jaw 26 reaches a position where the proximal end of the slot 320 approaches the pin 406, the jaw begins to rotate more and translate less as seen in FIG. 4b. When the jaw 26 is in the position where the proximal end of the slot 320 engages the pin 406, the jaw ceases to translate and rotates to the fully open position shown in FIG. 5.

Starting now from the fully open position shown in FIG. 5, which the jaws assume when the lever is moved farthest away from the handle, FIGS. 5a and 5b illustrate how the movable jaw translates and rotates to the fully closed position shown in FIG. 4. It should be noted that when the jaws are fully open, the movable jaw 26 is located such that the pin 406 is at the proximal end of the slot 320. As seen in FIG. 5a, when the pull wire 14 is moved in the proximal direction, the jaw 26 is also moved proximally with the slot 320 sliding over the pin 406. Due to the curvature of the slot 320, the jaw 26 is also slightly rotated toward the jaw 22. As the jaw 26 reaches a position where the midpoint of the slot 320 approaches the pin 406, the jaw begins to rotate more and translate less as seen in FIG. 5b. Due to the combined translational and rotational movement of the jaw 26, the buck tooth 340 acts like a scoop pulling tissue toward the opening in the stationary jaw 22. Simultaneously, the teeth 350 on the side walls of the jaw 26 cut the tissue which is scooped into the opening of the stationary jaw. In addition to scooping, the distal location of the buck tooth 340 gives it a great mechanical advantage in cutting through the tissue being sampled.

It should be appreciated by those skilled in the art that the stationary jaw 22 of the invention essentially functions as a die, while the movable jaw 26 functions as a dual purpose punch, with the side rows of sharp teeth 350 for punching/cutting through the sampled tissue, and the distal buck tooth 340 for cutting and scooping the sampled tissue. It will also be appreciated that the sampled tissue will be stored in the basket portion 224 of the stationary jaw 22. As the basket portion of the stationary jaw 22 has multiple small openings 234, more room is created for the storing of biopsy samples, as the samples can extend at least partially through the openings 234 without falling through and fluid in the sampled tissue is free to drain through the openings in the basket.

Figure 6:
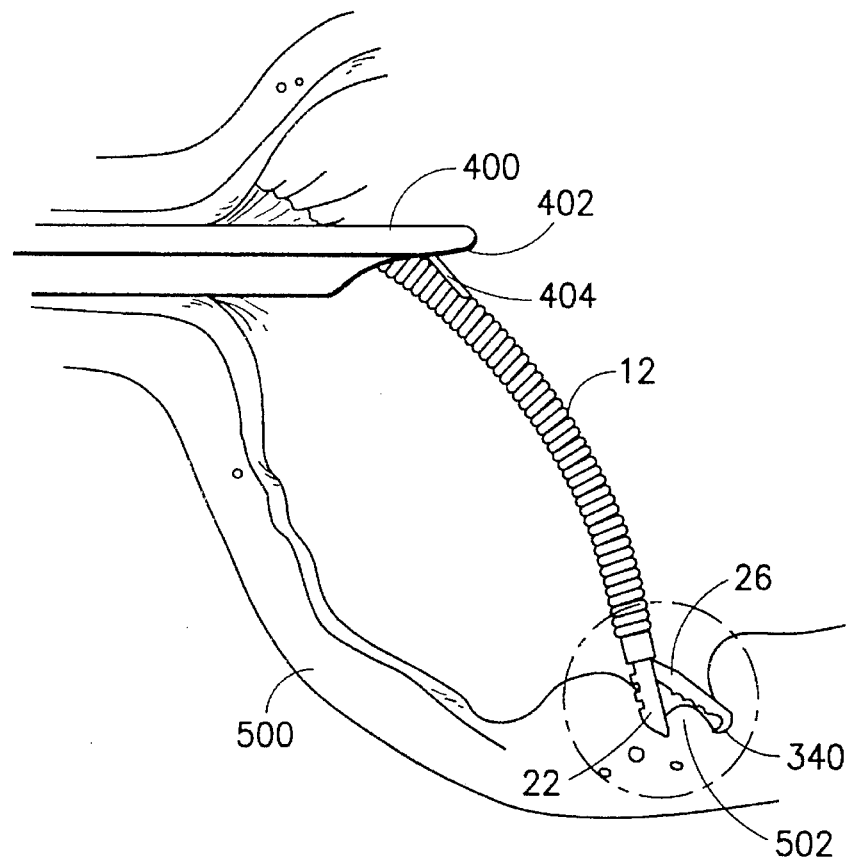
FIG. 6 is a perspective view of the distal end of the biopsy forceps of the invention extending from a deflecting cannula and grasping a portion of the wall of a bladder.
Figure 6A:
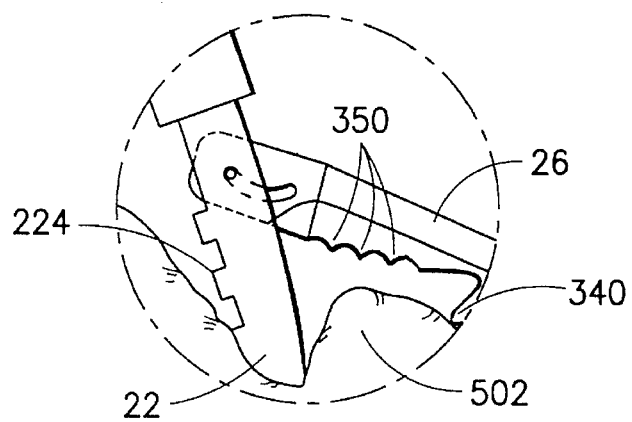
FIG. 6a is an enlarged view of a portion of FIG. 6.

From the foregoing and now with reference to FIGS. 6 and 6a, it will be appreciated that the biopsy forceps according to the invention significantly facilitates the taking of biopsy samples from the wall of a bladder 500. The forceps according to the invention are preferably delivered to the biopsy site through a cannula 400 having a distal end 402 incorporating a deflector 404. The movable jaw 26 is rotated to the open position. Using the deflector 404 of the cannula 400 and by advancing the coil 12 through the cannula, the jaws 22, 26 are brought in contact with the wall of the bladder 500 so that a tissue portion 502 of the bladder wall is engaged between the jaws. The actuator lever is pressed toward the handle of the actuators (FIG. 1) causing the movable jaw to move as described above. The distal buck tooth 340 of the movable jaw 26 digs into the tissue portion 502 and pulls it into the opening of the stationary jaw 22 while severing it. As the movable jaw continues to close, the side teeth 350 cut the sides of the tissue portion 502 and it is captured in the basket portion 224 of the stationary jaw 22. Due to the size of the basket portion and its draining openings, several tissue samples may be taken before the forceps are withdrawn from the biopsy site.

There has been described and illustrated herein a multiple sample urological biopsy forceps instrument. While a particular preferred embodiment of the invention has been described, it is not intended that the invention be limited thereto, as it is intended that the invention be as broad in scope as the art will allow and that the specification be read likewise. Thus, while particular dimensions have been disclosed in reference to the movable and stationary jaws, it will be appreciated that the jaws could assume other dimensions. Also, while a particular linkage means for linking the movable jaw to the pull wire has been disclosed, it will be understood that other linkage means can be used. For example, and not by way of limitation, instead of using a pull wire with a flat terminal portion having a throughhole, a pull wire with a T-shaped or a jogged distal end could be used. Further, while a particularly arranged biopsy sample basket in the stationary jaw has been disclosed, other designs may be used as well. For example, while several interspersed arcuate strips have been disclosed as forming the bottom of the stationary jaw, a closed bottom with several circular openings may also be used. Furthermore, while particular side cutting teeth and a buck tooth have been disclosed, it will be understood that other tooth configurations can be similarly used. For example, while three teeth on each row of teeth and an angled back buck tooth have been disclosed, additional teeth may be added to the rows of teeth and the buck tooth may assume a position more perpendicular to the longitudinal axis. Also, as mentioned above, the biopsy forceps of the invention may be used in an endoscopic instrument having a rigid tube and push rod rather than a flexible coil and pullwire. It will therefore be appreciated by those skilled in the art that yet other modifications could be made to the provided invention without deviating from its spirit and scope as so claimed.

We claim:

1. A biopsy forceps surgical instrument comprising:
   a) a hollow tube having a proximal and a distal end;
   b) a control member having a proximal and a distal end and extending through said hollow tube;
   c) an actuator coupled to said proximal end of said tube and said proximal end of said control member for imparting translational movement to said control member relative to said hollow tube;
   d) a stationary jaw coupled to said distal end of said tube, said stationary jaw having a longitudinal axis and a pin substantially perpendicular to said longitudinal axis; and
   e) a scooping movable jaw having an arcuate slot through which said pin extends, such that said movable jaw is pivotally coupled to said stationary jaw, said movable jaw being coupled to said distal end of said control member so that translational movement of said control member causes both translational and rotational movement of said movable jaw relative to said stationary jaw such that said movable jaw scoops a biopsy sample into said stationary jaw.

2. A surgical instrument according to claim 1, wherein:
said stationary jaw has a bottom surface having a plurality of openings therein.

3. A surgical instrument according to claim 2, wherein:
said stationary jaw has a longitudinal axis, said plurality of openings in said bottom surface of said stationary jaw are defined by a plurality of arcuate strips arranged substantially perpendicular to said longitudinal axis of said stationary jaw.

4. A surgical instrument according to claim 1, wherein:
said movable jaw further has a first severing surface and a distal severing tooth, and said movable jaw and said stationary jaw being arranged such that when said movable jaw is in a closed position relative to said stationary jaw, said first severing surface of said movable jaw is located inside said stationary jaw and said distal severing tooth of said movable jaw is located outside said stationary jaw.

5. A surgical instrument according to claim 4, wherein:
said movable jaw has a pair of parallel sides which define said first severing surface, said distal severing tooth is substantially perpendicular to said first severing surface and is angled toward the proximal end of the movable jaw.

6. A surgical instrument according to claim 1, wherein:
said movable jaw has a gouged interior defining a roof palate.

7. A biopsy forceps surgical instrument comprising:
   a) a hollow tube having a proximal and a distal end;
   b) a control member having a proximal and a distal end and extending through said hollow tube;

c) an actuator coupled to said proximal end of said tube and said proximal end of said control member for imparting translational movement to said control member relative to said hollow tube;

d) a stationary jaw coupled to said distal end of said tube, said stationary jaw having a pair of sidewalls defining an upper opening; and e) a movable jaw rotationally coupled to said stationary jaw, said movable jaw having a pair of sidewalls defining two rows of cutting teeth and a distal wall defining a single cutting tooth which is substantially perpendicular to said sidewalls of said movable jaw, wherein said movable jaw and said stationary jaw are arranged such that when said movable jaw is in a closed position relative to said stationary jaw, said two rows of cutting teeth are located inside said stationary jaw and said single cutting tooth is located outside and adjacent to the distal end of said stationary jaw.

8. A surgical instrument according to claim 7, wherein:
said stationary jaw has a bottom portion with at least one drainage opening.

9. A surgical instrument according to claim 7, wherein:
said stationary jaw has an integral clevis portion within which said movable jaw is coupled to said stationary jaw.

10. A surgical instrument according to claim 7, wherein:
said movable jaw has a gouged interior defining a roof palate.

11. A surgical instrument according to claim 10, wherein:
said roof palate has a relatively narrow and shallow distal portion and a relatively deep and wide proximal portion.

12. A surgical instrument according to claim 9, wherein:
said distal cutting tooth is angled in a proximal direction.

13. A biopsy forceps surgical instrument comprising:

a) a hollow tube having a proximal and a distal end;

b) a control member having a proximal and a distal end and extending through said hollow tube;

c) an actuator coupled to said proximal end of said tube and said proximal end of said control member for imparting translational movement to said control member relative to said hollow tube;

d) a stationary jaw coupled to said distal end of said tube, said stationary jaw having a pair of sidewalls defining an upper opening and a bottom portion having a plurality of drainage openings; and e) a movable jaw rotationally coupled to said stationary jaw and to said distal end of said control member, said movable jaw having a pair of sidewalls defining two rows of cutting teeth, a gouged interior defining a roof palate, and a distal tooth having a free end which is angled in a proximal direction when the movable jaw is in a closed position relative to the stationary jaw.

14. A surgical instrument according to claim 13, wherein:
said stationary jaw has an integral clevis within which said movable jaw is coupled to said stationary jaw.

15. A surgical instrument according to claim 13 wherein:
said plurality of drainage openings are defined by a plurality of parallel arcuate strips.

16. A surgical instrument according to claim 13, wherein:
said roof palate has a conic section.

17. A surgical instrument according to claim 13, wherein:
said movable jaw has a split proximal end defining two spaced apart walls within which said movable jaw is coupled to said distal end of said control member.

18. A surgical instrument according to claim 13, wherein:
said movable jaw has a distal tooth which extends between said sidewalls of said movable jaw.

19. A surgical instrument according to claim 18, wherein:
said movable jaw is movable from and opened position to a closed position and when in said closed position, said two rows of cutting teeth are received in said opening of said upper opening of said stationary jaw and said distal tooth resides outside and adjacent to the distal end of said stationary jaw.

* * * * *